United States Patent
Hinden-Kuhles et al.

(10) Patent No.: US 11,771,793 B2
(45) Date of Patent: Oct. 3, 2023

(54) MALODOR REDUCTION IN AIR CARE APPLICATIONS

(71) Applicant: Agilex Flavors and Fragrances, Inc., Piscataway, NJ (US)

(72) Inventors: Natalie L. Hinden-Kuhles, Somerville, NJ (US); Margaret C. Shine, Fairlawn, NJ (US); Thomas N. Siedel, West Caldwell, NJ (US); Viktoria M. Korosi, New York, NY (US); Nicole Oram, Raritan, NJ (US); Matthias A. Guentert, Ridgewood, NJ (US); Alice A. Rebeck, Hillsborough, NJ (US)

(73) Assignee: AGILEX FLAVORS AND FRAGRANCES, INC., Piscataway, NJ (US)

( * ) Notice: Subject to any disclaimer, the term of this patent is extended or adjusted under 35 U.S.C. 154(b) by 572 days.

(21) Appl. No.: 16/614,158

(22) PCT Filed: May 17, 2018

(86) PCT No.: PCT/US2018/033148
§ 371 (c)(1),
(2) Date: Nov. 15, 2019

(87) PCT Pub. No.: WO2018/213551
PCT Pub. Date: Nov. 22, 2018

(65) Prior Publication Data
US 2021/0402035 A1    Dec. 30, 2021

Related U.S. Application Data

(60) Provisional application No. 62/507,865, filed on May 18, 2017.

(51) Int. Cl.
| | | |
|---|---|---|
| *A61L 9/012* | (2006.01) | |
| *A61L 9/01* | (2006.01) | |
| *A61L 9/14* | (2006.01) | |
| *A61L 9/04* | (2006.01) | |
| *A61L 9/12* | (2006.01) | |
| *A61L 101/36* | (2006.01) | |

(52) U.S. Cl.
CPC ............ *A61L 9/048* (2013.01); *A61L 9/012* (2013.01); *A61L 9/127* (2013.01); *A61L 9/14* (2013.01); *A61L 2101/36* (2020.08); *A61L 2209/134* (2013.01)

(58) Field of Classification Search
CPC .......... A61L 9/048; A61L 9/012; A61L 9/127; A61L 9/14; A61L 2101/36; A61L 2209/134
See application file for complete search history.

(56) References Cited

U.S. PATENT DOCUMENTS

| | | |
|---|---|---|
| 6,253,710 B1 * | 7/2001 | Ward |
| 2011/0045983 A1 | 2/2011 | Healy et al. |
| 2012/0097754 A1 | 4/2012 | Vlad et al. |
| 2013/0090390 A1 | 4/2013 | Singer et al. |
| 2013/0183261 A1 | 7/2013 | Harada et al. |
| 2016/0089467 A1 * | 3/2016 | Wetterer |

FOREIGN PATENT DOCUMENTS

| | | | |
|---|---|---|---|
| CN | 103030538 A | | 4/2013 |
| CN | 106668921 A | | 5/2017 |
| EP | 0 462 605 A2 | * | 12/1991 |
| GB | 2 409 161 | * | 6/2005 |
| JP | 2003073690 A | | 3/2003 |
| KR | 20130102468 A | | 9/2013 |
| WO | 2011143242 A2 | | 11/2011 |
| WO | 2017015173 A1 | | 1/2017 |
| WO | 2017055603 A1 | | 4/2017 |

OTHER PUBLICATIONS

"Living Area Explained" (accessed on Nov. 2, 2022 from https://saterdesign.com/blogs/news/living-area-explained, pp. 1-2) (Year: 2022).*
International Search Report and Written Opinion for International Application No. PCT/US2018/033148, dated Aug. 21, 2018. 14 pages.
Katz et al., "Odor Elimination Testing Never Smelled Better", Perfumer & Flavorist, Published Aug. 2016, pp. 38-39, vol. 41.

* cited by examiner

*Primary Examiner* — Alma Pipic (57) ABSTRACT

Described herein are compositions for malodor reduction in various air care applications.

4 Claims, 7 Drawing Sheets

MALODOR REDUCTION IN AIR CARE APPLICATIONS

CROSS REFERENCE TO RELATED APPLICATIONS

The present application is a U.S. National Phase Application of PCT/US2018/033148, filed on May 17, 2018 which claims the benefit of priority to U.S. Provisional Patent Application Ser. No. 62/507,865, filed on May 18, 2017, the entire contents of which are hereby incorporated by reference in their entirety.

FIELD

The present invention relates to malodor reducing and odor freshening compositions in air care applications.

BACKGROUND

The air care segment in perfumery has been one of the fastest growing market segments in recent years. Increasingly, consumers seek for air care products that help to maintain a clean and fresh atmosphere in the various rooms of their homes. There are many different types of air care products which relate mostly to the fact that there are different types of malodors to tackle. This ranges from typical aerial kitchen malodors, malodors in living rooms: either in the air, or in carpets and wall paper, to malodors in bathrooms.

Although the typical use of these air care products may be at home there is also the need for effective products in outside-the-home applications (e.g., industrial, restaurant and hospital kitchens; office rooms; industrial, restaurant and hospital bathrooms; mobile portable toilets; public and private transportation; sports facilities and waste management).

The main sub-categories of these air care products are scented candles, scented wax melts, gels, passive air fresheners, active air fresheners, and aerosol and non-aerosol sprays. Manufacturers of products for controlling/reducing malodor often utilize ingredients for malodor reduction that may be effective at reducing, but not necessarily eliminating, malodor. In many products, scented perfumes are used to help mask malodors, however malodor may still remain and become noticeable once again after the potency of the scented perfume wears off. Hence these perfumes are either augmented by malodor active ingredients and/or some of the common perfume ingredients take on a functional role as well in the finished product.

SUMMARY

Aspects of the present disclosure relate to malodor reducing and odor freshening compositions that include a malodor reducing component as well as one or several freshening fragrance components. Methods of use thereof are also provided. Such odor improving compositions may be used to reduce malodor and boost the fresh odor in air care applications, such as in kitchens, living rooms, offices, bathrooms, lobbies, trash rooms and others.

In certain aspects, a composition for malodor reduction in air care includes lauryl methacrylate and one or several freshening fragrance components.

In certain aspects, a method of reducing malodor in air includes applying a composition (e.g., one of the compositions described herein) for malodor reduction air care applications, such as in kitchens, living rooms, offices, bathrooms, lobbies, trash rooms and others.

In certain aspects, perfume compositions for reducing malodors in air care applications, such as in kitchens, living rooms, offices, bathrooms, lobbies, trash rooms and others include a malodor reducing component and a freshening fragrance component. For example, the malodor reducing component may comprise lauryl methacrylate.

In one aspect, the alkyl group is chosen from a straight chain $C_{1-10}$ alkyl group. In another aspect, the alkyl group is chosen from a branched chain $C_{1-10}$ alkyl group. In another aspect, the alkyl group is chosen from a straight chain $C_{1-6}$ alkyl group. In another aspect, the alkyl group is chosen from a branched chain $C_{1-6}$ alkyl group. In another aspect, the alkyl group is chosen from a straight chain $C_{1-4}$ alkyl group. In another aspect, the alkyl group is chosen from a branched chain $C_{1-4}$ alkyl group. In another aspect, the alkyl group is chosen from a straight or branched chain $C_{2-4}$ alkyl group. Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, decyl, and the like. Non-limiting exemplary $C_{1-4}$ alkyl groups include methyl, ethyl, propyl, isopropyl, butyl, sec-butyl, tert-butyl, and iso-butyl.

DETAILED DESCRIPTION

In the following description, reference is made to specific aspects which may be practiced, which is shown by way of illustration. These aspects are described in detail to enable those skilled in the art to practice the invention described herein, and it is to be understood that other aspects may be utilized and that logical changes may be made without departing from the scope of the aspects presented herein. The following description of example aspects is, therefore, not to be taken in a limited sense, and the scope of the various aspects presented herein is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

For the purpose of the present disclosure, the terms "alkyl" and "hydrocarbon" as used alone or as part of another group refers to a straight- or branched-chain aliphatic hydrocarbon containing one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.).

For the purpose of the present disclosure, the term "amino" or "amine" as used alone or as part of another group refers to —$NH_2$.

Some of the compounds disclosed herein may contain one or more asymmetric centers and may thus give rise to enantiomers, diastereomers, and other stereoisomeric forms. The present disclosure is meant to encompass the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present disclosure as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "about," as used herein in connection with a measured quantity, refers to the normal variations in that measured quantity, as expected by the skilled artisan making the measurement and exercising a level of care commensurate with the objective of measurement and the precision of the measuring equipment.

Certain aspects are directed toward a composition for malodor reduction in air care applications, the composition including a malodor reducing component and a freshening fragrance component.

In certain aspects, the malodor reducing component includes n-dodecyl methacrylate (lauryl methacrylate). Lauryl methacrylate is commonly utilized as part of a polymeric or copolymeric composition (e.g., poly(lauryl methacrylate) in detergents). In the disclosed aspects, lauryl methacrylate is utilized in its monomeric form to reduce malodor.

In certain aspects, the freshening fragrance component includes one or more fragrance compounds, which may include mixtures of volatile aldehydes, esters, ketones, alcohols, hydrocarbons, lactones, and nitriles. It is known that volatile aldehydes can neutralize malodors in the vapor and/or liquid phases via chemical reactions. Volatile aldehydes may react with amine-based odors, following the path of Schiff-base formation. Volatile aldehydes may also react with sulfur-based odors, forming thiol acetals, hemi-thiol acetals, and thioesters in the vapor and/or liquid phases. Alcohols may react chemically with malodorous aldehydes.

In addition, many aldehydes and other fragrance materials are also strong odorants that may help to mask the malodorous components and hence help to freshen the air in the room by using the respective air care products.

Exemplary volatile fragrance materials which may be used as a malodor freshening component include, but are not limited to a freshening fragrance component selected from a group consisting of Adoxal (2,6,10-Trimethyl-9-undecenal), Aldehyde C-8, Aldehyde C-9, Aldehyde C-10, Aldehyde C-11, Aldehyde C-12, Aldehyde C-14, Aldehyde C-16, Aldehyde C-18, Allyl amyl glycolate, Allyl cyclohexyl propionate, Allyl heptanoate, Amyl acetate, Ambretone, Ambroxan, Amyl salicylate, Bacdanol, Basil oil, Benzaldehyde, Borneol, Bourgeonal (4-t-butylbenzenepropionaldehyde), Buchu Leaf oil, Cashmeran, Cedar Leaf oil, Cinnamic alcohol, Cinnamic aldehyde, Citral, Citrathal, Citronellal (3,7-dimethyl 6-octenal), Citronellol, Citronellyl nitrile, Citronitrile, Clonal, Coumarin, Cyclal (2,4-dimethyl-3-cyclohexen-1-carbaldehyde), Cyclacet, Cyclamen aldehyde (cyclamal), Cyclaprop, Cymal, Cyclosal, Cyclopentadecanone, Damascenone, delta-Damascone, gamma-Declalactone, trans-2-Decenal, cis-4-Decenal, Diethyl malonate, Dihydrojasmone, Dihydromyrcenol, Dihydromyrcenyl acetate, Dimethyl benzyl carbonyl butyrate, Dimetol, Dioctyl adipate, trans-2-Dodecenal, Dupical, Dynascone, Ethyl acetate, Ethyl butyrate, Ethyl linaly acetate, Ethyl vanillin, Ethyl linalyl acetate, Ethylene brassylate, Ethyl butyrate, Ethyl caprylate, Eugenol, Florhydral (3-(3-Isopropyl-phenyl)-butyraldehyde), Floralozone, Florhydral, Fructone, Galaxolide, Geraniol, Geranium oil, Geranyl acetate, Hedione, Helional (alpha-methyl-3,4-(methylenedioxy)-hydrocinnamaldehyde), Hercolyn D, Hexadecanolide, cis-3-Hexenyl acetate, Hexyl acetate, Hexyl cinnamic aldehyde, Hexyl salicylate, Hydrocinnamaldehyde (3-phenylpropanal), Hydroxycitronellal, Hydroxycitronellol, Indoflor, alpha-Ionone, beta Ionone, Isobutylquinoline, Iso cyclo citral, Iso E Super, Isoeugenol, Isofragrarone, Karanal, Lavender oil, Lavendin oil, Lime aldehyde (alpha-methyl-p-isopropyl phenyl propyl aldehyde), Limonene, Lilial (2-methyl-4-t-butylphenyl)propanal), Linalool, Linalyl acetate, Linalooloxide, Lyral (4-(4-hydroxy-4-methylpentyl)-3-cyclohexene-1-carboxaldehyde), Manzanate, Melonal (2,6-Dimethyl-5-Heptenal), Methoxy Melonal (6-Methoxy-2,6-Dimethylheptanal), Methyl acetophenone, Methyl anthranilate, alpha-Methyl ionone, gamma-Methyl ionone, Methyl salicylate, Methyl Nonyl Acetaldehyde, 2-Methyl-undecenal (C-12 MNA), Myrac aldehyde, 2,6-Nonadienal, 2,6-Nonadienol, Orange terpenes, Orange oil, Oxane, Oxoctaline formate, Oxyphenylon, Ozonil, Patchouli oil, Petitgrain oil, Petiole, Phenylacetaldehyde, Phenylethanol, Pino acetaldehyde, Precyclemone B, Polysantol, Raspberry ketone, Rose crystals, Rosemary oil, Scentenal, Sinensal, Spirogalbanone, Styrallyl acetate, Tangerinol, Tetrahydrolinalyl acetate, Tetrahydromyrcenol, para-Tolylaldehyde, Tricyclodecylidenebutanal Tridecene-2-nitrile, Triplal, Vanillin, Vernaldehyde, Vertocitral (2,4-dimethyl-3-cyclohexene-1-carboxaldehyde), Verdox, Vertenex, Violet nitrile, Yara Yara, Ylang, as well as combinations thereof.

In certain aspects, the freshening fragrance component comprises one or more fragrance compounds, which may include mixtures of volatile aldehydes, esters, ketones, alcohols, lactones, ethers, hydrocarbons, lactones, nitriles, and other chemical classes. Volatile aldehydes can neutralize malodors in the vapor and/or liquid phases via chemical reactions. Volatile aldehydes may react with amine-based odors, following the path of Schiffbase formation. Volatile aldehydes may also react with sulfur-based odors, forming thiol acetals, hemi-thiol acetals, and thioesters in the vapor and/or liquid phases. Alcohols may react chemically with malodorous aldehydes. In addition, many aldehydes and other fragrance materials are also strong odorants that may help to mask the malodorous components and hence help to freshen the odor of the surrounding air.

In certain aspects, the freshening fragrance component comprises one or more of aldehydes, esters, or alcohols. In certain aspects, the one or more of aldehydes, esters, or alcohols are present from 1% to 95% by weight in the composition. In one aspect, one or more esters may be present from 5% to 80%, from 10% to 70%, from 20% to 60%, or from 30% to 60% by weight in the composition. In one aspect, one or more aldehydes may be present from 5% to 55%, from 10% to 50%, from 20% to 45%, or from 30% to 40% by weight in the composition. In one aspect, one or more alcohols may be present from 5% to 70%, from 10% to 60%, from 20% to 50%, or from 30% to 40% by weight in the composition. In one aspect, one or more ketones may be present from 0.1% to 15%, from 0.5% to 10%, from 1% to 7.5%, or from 2% to 5% by weight in the composition. In one aspect, one or more lactones may be present from 0.1% to 15%, from 0.5% to 10%, from 1% to 7.5%, or from 2% to 5% by weight in the composition. In one aspect, one or more nitriles may be present from 0.1% to 10%, from 0.5% to 7.5%, from 1% to 5%, or from 2% to 5% by weight in the composition.

The present invention is best illustrated but is not limited to the following examples.

EXAMPLES

Example 1: Malodor Reduction Using Compositions According to Certain Aspects Presented Herein In order to assess the reduction of the kitchen malodor in an early experimental set up (part 1) a malodor reference (garlic composition) was placed on cotton balls in 2 oz. wide mouth jars. Fragrance samples in accordance with embodiments described herein were made by adding 7% fragrance to a stearate gel base, 25 grams were put into 2 oz. wide mouth jars. A rating system of 0 (no malodor) to 10 (high level of malodor) was applied. The sensory panel consisted of 15 people on average. By using various fragrance formulations with the same malodor accords the reduction of malodor was sensorially assessed at a significant amount of 27-42%.

In order to assess the reduction of the bathroom malodor in an early experimental set up (part 1) the malodor reference (skatol) was placed on cotton balls in 2 oz. wide mouth jars. Fragrance samples were made by adding 7% fragrance to a gel base, 25 grams were put into 2 oz. wide mouth jars. A rating system of 0 (no malodor) to 10 (high level of malodor) was applied. The sensory panel consisted of 15 people on average. By using various fragrance formulations with the same malodor accords the reduction of malodor was sensorially assessed at a significant amount and more consistently of 42-45%.

In further experiments to assess the reduction of the kitchen malodor in the early experimental set up (part 2) the malodor reference (garlic composition) was placed on cotton balls in 2 oz. wide mouth jars. Fragrance samples were made by adding 7% fragrance to a Stearate gel base, 25 grams were put into 2 oz. wide mouth jars. A rating system of 0 (no malodor) to 10 (high level of malodor) was applied. The sensory panel consisted of 15 people on average. By using various fragrance formulations with the different malodor accords the reduction of malodor was sensorially assessed at a significant and consistent amount of 53-63%.

In further experiments to assess the reduction of the bathroom malodor in the early experimental set up (part 2) the malodor reference (skatol) was placed on cotton balls in 2 oz. wide mouth jars. Fragrance samples were made by adding 7% fragrance to gel base, 25 grams were put into 2 oz. wide mouth jars. A rating system of 0 (no malodor) to 10 (high level of malodor) was applied. The sensory panel consisted of 15 people on average. By using various fragrance formulations with the different malodor accords the reduction of malodor was sensorially assessed at a significant and consistent amount of 49-57%.

In yet further experiments to assess the reduction of the kitchen malodor in the early experimental set up (part 3) and after optimizing the malodor fragrance accords the malodor reference (garlic composition) was placed on cotton balls in 2 oz. wide mouth jars. Fragrance samples were made by adding 7% fragrance to a stearate gel base, 25 grams were put into 2 oz. wide mouth jars. A rating system for malodor strength of 0 (no malodor) to 10 (high level of malodor) was applied. At the same time a rating system for strength of the fragrance odor of 0 (no fragrance) to 10 (high level of fragrance) was applied. The sensory panel consisted of 15 people on average. By using various fragrance formulations with the different malodor accords this time the panelists were asked to assess the strength of the fragrance and the strength of the malodor. They smelled the malodor control first, and then the samples in random order. Considering the level of malodor in the control to be rated as 10, panelists were asked to rate the level of malodor independent of fragrance in the samples. The panelists were also asked to smell the control prior to each fragrance sample. In these experiments the malodor reduction was sensorially assessed at a significant amount of 67-72% while the fragrance strength was retained at 62-69%.

Figure 1:
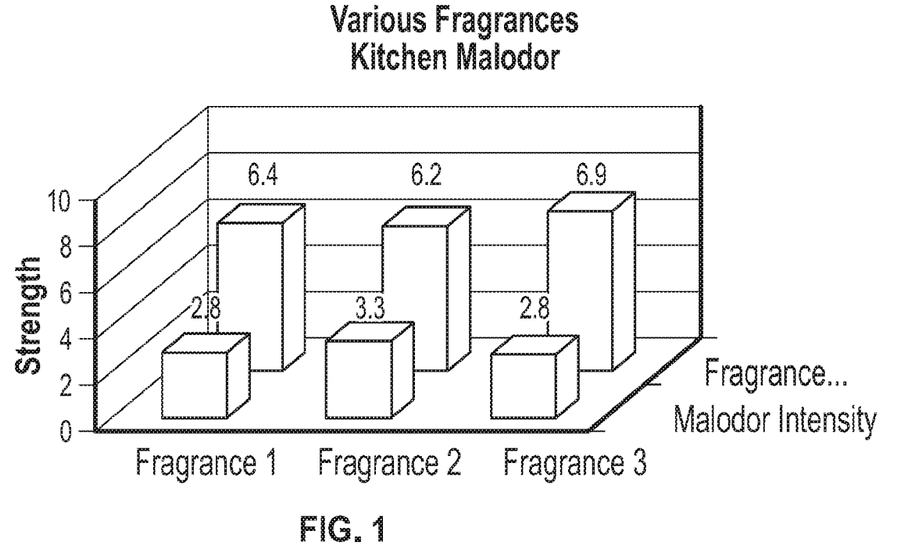
FIG. 1 shows an exemplary experimental set up and the observed malodor reduction, as reported by a sensory panel.

FIG. 1 shows exemplarily how the set up was conducted and the panel rated the malodor reduction.

The fragrance samples were generated as follows:
1. 7% Fragrance accord containing 0.1 wt % lauryl methacrylate ("Fragrance 1" in FIG. 1); This does have Neutrazine 0.1%
2. 85 wt % Fragrance accord containing 0.1 wt % lauryl methacrylate+15 wt % of a first malodor counteracting accord; and
3. 85 wt % Fragrance accord containing 0.1 wt % lauryl methacrylate+15 wt % of a second malodor counteracting accord ("Fragrance 3" in FIG. 1).

The first and second malodor counteracting accords comprised of aromachemicals designed to reduce the malodor.

In yet further experiments to assess the reduction of the bathroom malodor in the early experimental set up (part 3) and after optimizing the malodor fragrance accords the bathroom reference (skatol) was placed on cotton balls in 2 oz. wide mouth jars. Fragrance samples were made by adding 7% fragrance to a stearate gel base, 25 grams were put into 2 oz. wide mouth jars. A rating system for malodor strength of 0 (no malodor) to 10 (high level of malodor) was applied. At the same time a rating system for strength of the fragrance odor of 0 (no fragrance) to 10 (high level of fragrance) was applied. The sensory panel consisted of 15 people on average. By using various fragrance formulations with the different malodor accords this time the panelists were asked to assess the strength of the fragrance and the strength of the malodor. They smelled the malodor control first, and then the samples in random order. Considering the level of malodor in the control to be rated as 10, panelists were asked to rate the level of malodor independent of fragrance in the samples. The panelists were also asked to smell the control prior to each fragrance sample. In these experiments the malodor reduction was sensorially assessed at a significant amount of 52-58% while the fragrance strength was retained at 61-71%.

Figure 2:
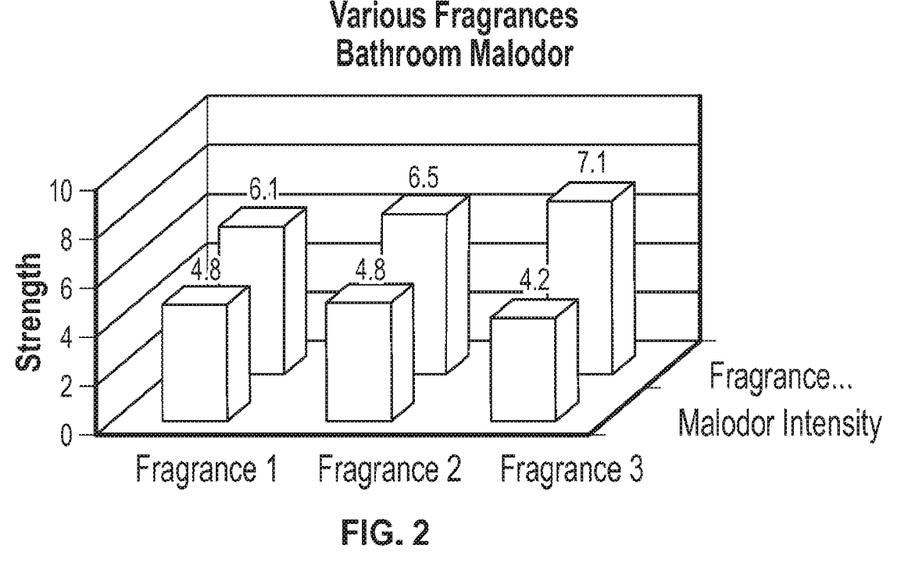
FIG. 2 shows an exemplary experimental set up and the observed malodor reduction, as reported by a sensory panel.

FIG. 2 shows exemplarily how the set up was conducted and the panel rated the malodor reduction.

The fragrance samples were generated as follows:
1. 7% Fragrance accord containing 0.1 wt % lauryl methacrylate ("Fragrance 1" in FIG. 1); This does have Neutrazine 0.1%
2. 85 wt % Fragrance accord containing 0.1 wt % lauryl methacrylate+15 wt % of a first malodor counteracting accord; and
3. 85 wt % Fragrance accord containing 0.1 wt % lauryl methacrylate+15 wt % of a second malodor counteracting accord ("Fragrance 3" in FIG. 1).

The first and second malodor counteracting accords comprised of aromachemicals designed to reduce the malodor.

These early experiments show that overall the respective malodor accords as part of the final fragrance work significantly to reduce kitchen and bathroom malodor. They also show that while the fragrance odor is not perceived at its original strength anymore it is still perceived at a range of 61 to 71%. The conclusion from these experiments are interpreted in a way that the malodor reduction effect is achieved by the combination of active malodor reduction as well as 'masking' the malodor by strong fragrance materials.

Example 2: Malodor Reduction Using Compositions According to Certain Aspects Presented Herein Formulations were constructed as follows:
1. 7% Brushed Cotton fragrance containing 0.1 wt % lauryl methacrylate ("Original", left bar in FIG. 3, top panels);
2. 7% Brushed Cotton fragrance containing 0.1 wt % lauryl methacrylate+15 wt % of a first malodor counteracting ("Original+Accord 15%", middle bar in FIG. 3, top panels);
3. 7% Sparkling Citrus fragrance containing 0.1 wt % lauryl methacrylate ("Original", left bar in FIG. 3, middle panels);
4. 7% Sparkling Citrus fragrance containing 0.1 wt % lauryl methacrylate+15 wt % of a first malodor counteracting accord ("Original+Accord 15%", middle bar in FIG. 3, middle panels);
5. 7% Bamboo Rain fragrance containing 0.1 wt % lauryl methacrylate ("Original", left bar in FIG. 3, lower panels); and
6. 7% Bamboo Rain fragrance containing 0.1 wt % lauryl methacrylate+15 wt % of a first malodor counteracting accord ("Original+Accord 15%", middle bar in FIG. 3, lower panels).

Figure 3:
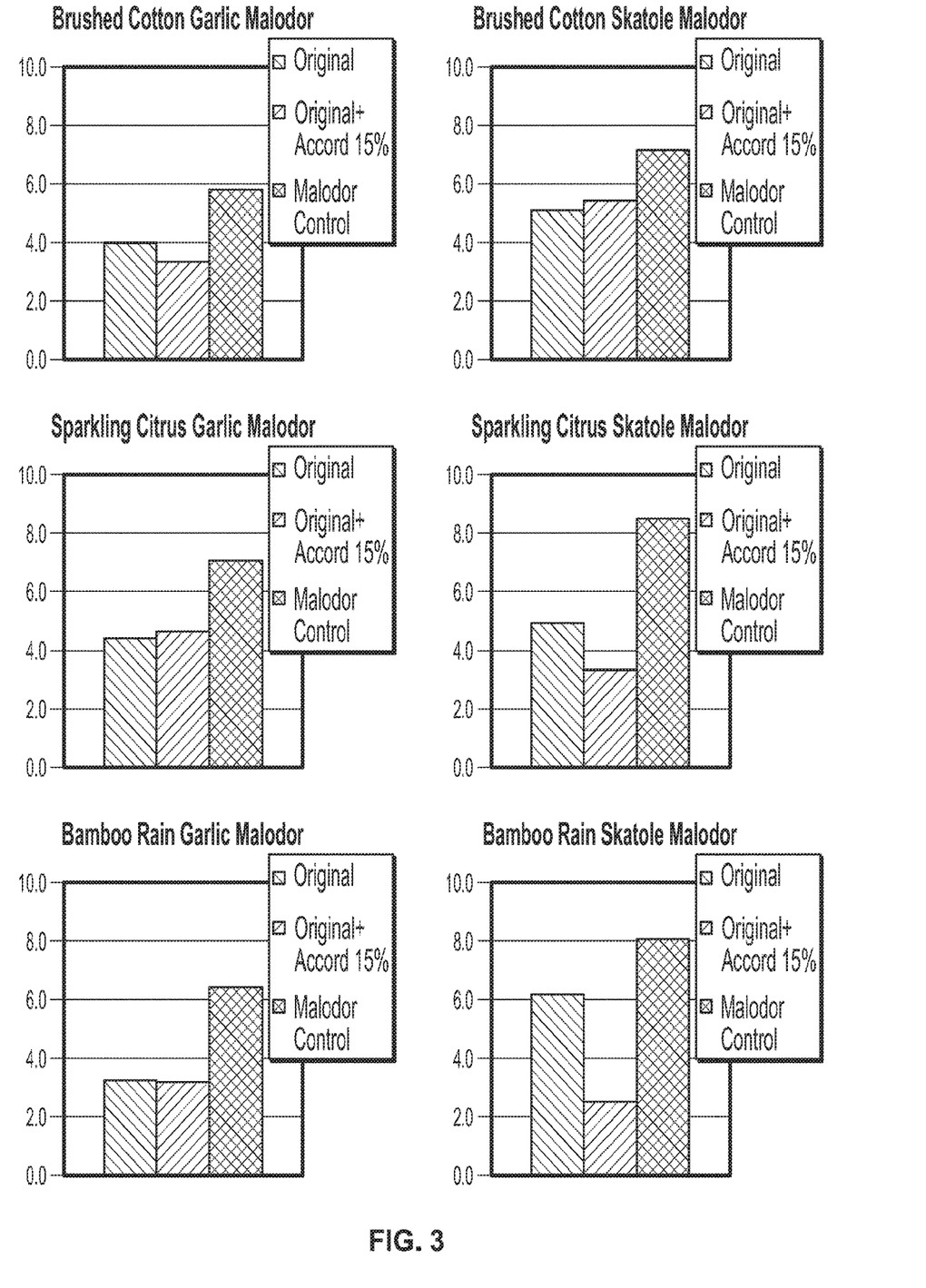
FIG. 3 shows sensory testing results, showing the reduction in perception of malodor using formulations according to certain aspects presented herein.

Samples were made by adding 7% fragrance to stearate gel base, 25 g was put into a 2 oz. wide mouth jar. A malodor formulation was placed on a cotton ball in a 2 oz wide mouth jar. Samples were placed in Rubbermaid bins alongside the malodor. The jars were opened for 2 hrs. prior to evaluation. The kitchen malodor tested comprised garlic oil (FIG. 3, left panels), and the bathroom malodor comprised a 10% w/w solution of skatole (FIG. 3, right panels). Samples 1 to 6 above were evaluated in the presence of 0.1 g malodor formulation. The control samples comprised 0.02 g kitchen malodor formulation or 0.05 g bathroom malodor formulation (right bars in FIG. 3 panels).

The first and second malodor counteracting accords comprised of aromachemicals designed to reduce the malodor.

Panelists were asked smell the malodor control then the samples in random order. They were asked to rate the level of malodor independent of fragrance level. They were also asked to rate the intensity of the malodor control. The results are shown in FIG. 3.

In all cases the malodor control had the highest rating despite being a fraction of the intensity level, showing that all the fragrance formulations reduced the perception of the malodor. In samples comprising the brushed cotton fragrance, the presence of the 0.1 wt % lauryl methacrylate in the fragrance did not appear to have an effect on the observed reduction in the perception of either kitchen or bathroom malodor, in that the magnitude of malodor reduction observed using formulation 1 above was similar to the magnitude of malodor reduction observed using formulation 2 above.

In contrast, in samples comprising the sparkling citrus fragrance, 0.1 wt % lauryl methacrylate appeared to enhance the reduction in the perception of the bathroom malodor by the malodor accord, in that the magnitude of the reduction in perception of the bathroom malodor observed by subjects with formulation 4 above, compared to the reduction in perception of the bathroom malodor observed by subjects with formulation 3 above. A similar enhancement of the reduction in the perception of the bathroom malodor was observed in the bamboo rain fragrances, in that the magnitude of the reduction in perception of the bathroom malodor observed by subjects with formulation 6 above, compared to the reduction in perception of the bathroom malodor observed by subjects with formulation 5 above.

Next, fragrance formulations containing 0.1 wt % lauryl methacrylate were tested with 25 wt % of a first malodor counteracting accord. Samples were placed in Rubbermaid bins along side the malodor. The malodor control was placed in the Rubbermaid bin alone. The jars were opened for 2 hours prior to evaluation. Panelists were asked smell the malodor control then the samples in random order. Considering the level of malodor in the control to be rated as 10, panelists were asked to rate the level of malodor independent of fragrance in the sample bins. Panelists were also asked to smell the control prior to each fragrance sample.

Figure 4:
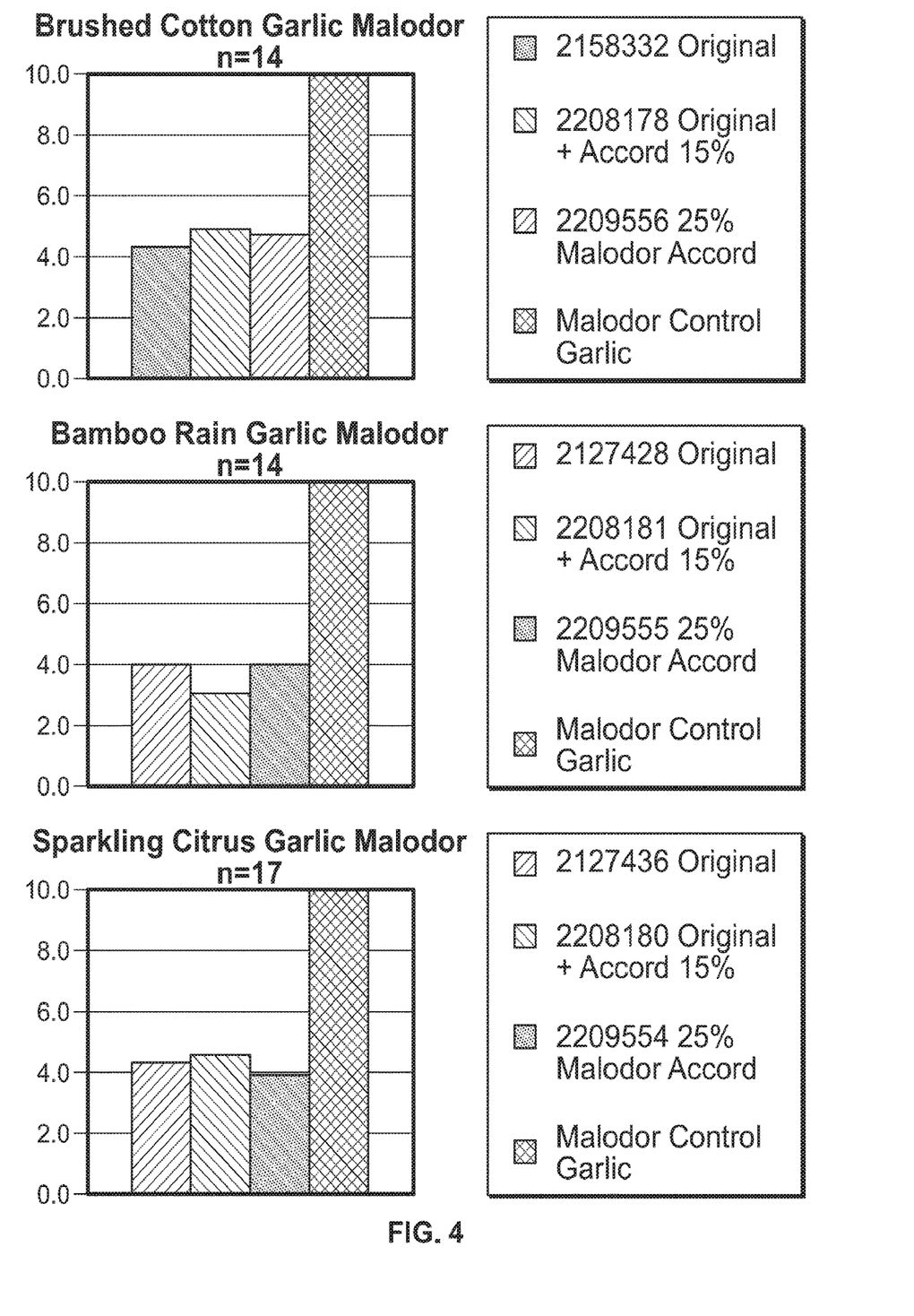
FIG. 4 shows sensory testing results, showing the reduction in perception of malodor using formulations according to certain aspects presented herein.

Formulations were constructed as follows:
1. 7% Brushed Cotton fragrance containing 0.1 wt % lauryl methacrylate ("Original", left bar in FIG. 4, top panels);
2. 7% Brushed Cotton fragrance containing 0.1 wt % lauryl methacrylate+15 wt % of a first malodor counteracting accord ("Original+Accord 15%", second bar from left in FIG. 4, top panels);
3. 7% Brushed Cotton fragrance containing 0.1 wt % lauryl methacrylate+25 wt % of a first malodor counteracting accord ("Original+Accord 15%", third bar from left in FIG. 4, top panels);
4. 7% Sparkling Citrus fragrance containing 0.1 wt % lauryl methacrylate ("Original", left bar in FIG. 4, middle panels);
5. 7% Sparkling Citrus fragrance containing 0.1 wt % lauryl methacrylate+15 wt % of a first malodor counteracting accord ("Original+Accord 15%", second bar from left in FIG. 4, middle panels);
6. 7% Sparkling Citrus fragrance containing 0.1 wt % lauryl methacrylate+25 wt % of a first malodor counteracting accord ("Original+Accord 15%", third bar from left in FIG. 4, middle panels);
7. 7% Bamboo Rain fragrance containing 0.1 wt % lauryl methacrylate ("Original", left bar in FIG. 4, lower panels);
8. 7% Bamboo Rain fragrance containing 0.1 wt % lauryl methacrylate+15 wt % of a first malodor counteracting accord ("Original+Accord 15%", second bar from left in FIG. 4, lower panels); and
9. 7% Bamboo Rain fragrance containing 0.1 wt % lauryl methacrylate+25 wt % of a first malodor counteracting accord ("Original+Accord 15%", third bar from left in FIG. 4, lower panels).

Samples were made by adding 7% fragrance to stearate gel base, 25 g was put into a 2 oz. wide mouth jar. A malodor formulation was placed on a cotton ball in a 2 oz wide mouth jar. Samples were placed in Rubbermaid bins alongside the malodor. The jars were opened for 2 hrs. prior to evaluation. The kitchen malodor tested comprised garlic oil (FIG. 4, left panels), and the bathroom malodor comprised a 10% w/w solution of skatole (FIG. 4, right panels). Samples 1 to 6 above were evaluated in the presence of 0.1 g malodor formulation. The control samples comprised 0.02 g kitchen malodor formulation or 0.05 g bathroom malodor formulation (right bars in FIG. 4 panels). The first and second malodor counteracting accords comprised of aromachemicals designed to reduce the malodor.

Panelists were asked smell the malodor control then the samples in random order. They were asked to rate the level of malodor independent of fragrance level. They were also asked to rate the intensity of the malodor control. The results are shown in FIG. 4.

In all cases the malodor control had the highest rating despite being a fraction of the intensity level, showing that all the fragrance formulations reduced the perception of the malodor. In samples comprising the brushed cotton fragrance, the presence of the 0.1 wt % lauryl methacrylate in the fragrance did not appear to have an effect on the observed reduction in the perception of either kitchen or bathroom malodor, in that the magnitude of malodor reduction observed using formulation 1 above was similar to the magnitude of malodor reduction observed using formulation 2 above.

In contrast, in samples comprising the sparkling citrus fragrance, 0.1 wt % lauryl methacrylate appeared to enhance the reduction in the perception of the bathroom malodor by the malodor accord, in that the magnitude of the reduction in perception of the bathroom malodor observed by subjects with formulations 5 and 6 above, compared to the reduction in perception of the bathroom malodor observed by subjects with formulation 4 above. A similar enhancement of the reduction in the perception of the bathroom malodor was observed in the bamboo rain fragrances, in that the magnitude of the reduction in perception of the bathroom malodor observed by subjects with formulations 8 and 9 above, compared to the reduction in perception of the bathroom malodor observed by subjects with formulation 7 above.

Example 3: Malodor Reduction Using Compositions According to Certain Aspects Presented Herein In an advanced experimental set up the qPOD® technology (Portable Olfactive Evaluation Devices patented by Q Research Solutions) was used. This qPOD® mobile scent tester evaluation tool with specialized air handling capabilities for fragrances and flavors attempts to mimic real life conditions for malodor assessments. It was recently described in Perfumer & Flavorist, 38, August 2016, 38-39. For the setup of the shown examples typically 4 of the qPOD® units were applied. In the first unit the respective pure malodor known by the panelists was assessed (100%). In the second unit the fragrance containing 0.1 wt % lauryl methacrylate unbeknownst to the panelists in the respective application was smelled. In the third unit the actual experiment (malodor+fragrance containing 0.1 wt % lauryl methacrylate) in the respective application was tested. And in the fourth unit the pure malodor again but this time unbeknownst to the panelists was smelled.

In order to assess the reduction of the kitchen malodor in the advanced experimental set up the complex pure malodor reference was placed in one of the qPOD® units. In the second unit a fragranced candle in burn mode (without malodor, comprising 5 wt % fragrance containing 0.1 wt % lauryl methacrylate) was placed. In the third unit the malodor was placed along with the fragranced candle (comprising 5 wt % fragrance containing 0.1 wt % lauryl methacrylate) in burn mode. In the fourth unit the pure malodor was placed again but this time unbeknownst to the panelists. It is important to note that this number was normalized to 100% and used as the reference line for any reduction. A rating system for the malodor of 0 (no malodor) to 10 (high level of malodor) as well as for the fragrance of 0 (no smell of fragrance) to 10 (strongest smell of fragrance) was applied. The sensory panel consisted of 15-20 people on average. There was a significant reduction by 58.3%. In this experiment the fragrance strength was assessed at 53.3%.

Figure 5:
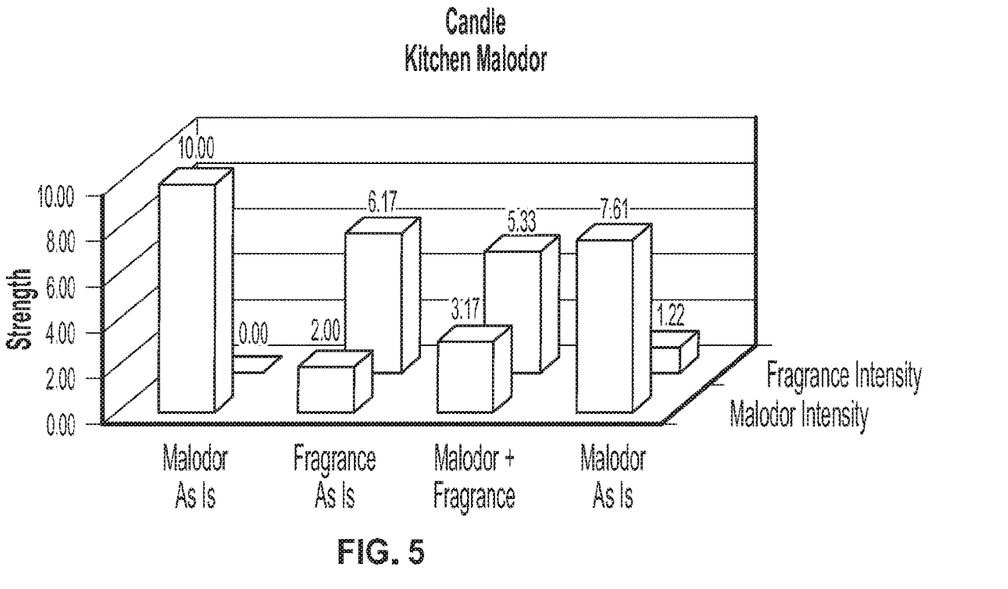
FIG. 5 shows an exemplary experimental set up and the observed malodor reduction, as reported by a sensory panel.

FIG. 5 shows exemplarily how the set up was conducted and the panel rated the malodor reduction. The pure malodor assessment (100%) known by the panelists is shown (left), as well as the pure fragrance (comprising 5 wt % fragrance containing 0.1 wt % lauryl methacrylate) (61.7%) unknown by the panelists as the second from left, the actual experiment as the third from left, and the pure malodor (76.1%) also unknown by the panelists on the right hand side. This number was normalized to 100% to calculate the reduction.

In order to assess the reduction of the bathroom malodor in the advanced experimental set up the complex pure malodor reference was placed in one of the qPOD® units. In the second unit the fragranced candle (comprising 5 wt % fragrance containing 0.1 wt % lauryl methacrylate) in burn mode (without malodor) was placed. In the third unit the malodor was placed along with the fragranced candle (comprising 5 wt % fragrance containing 0.1 wt % lauryl methacrylate) in burn mode. In the fourth unit the pure malodor was placed again but this time unbeknownst to the panelists. It is important to note that this number was normalized to 100% and used as the reference line for any reduction. A rating system for the malodor of 0 (no malodor) to 10 (high level of malodor) as well as for the fragrance of 0 (no smell of fragrance) to 10 (strongest smell of fragrance) was applied. The sensory panel consisted of 15-20 people on average. There was a significant reduction by 50.7%. In this experiment the fragrance strength was assessed at 47.2.

Figure 6:
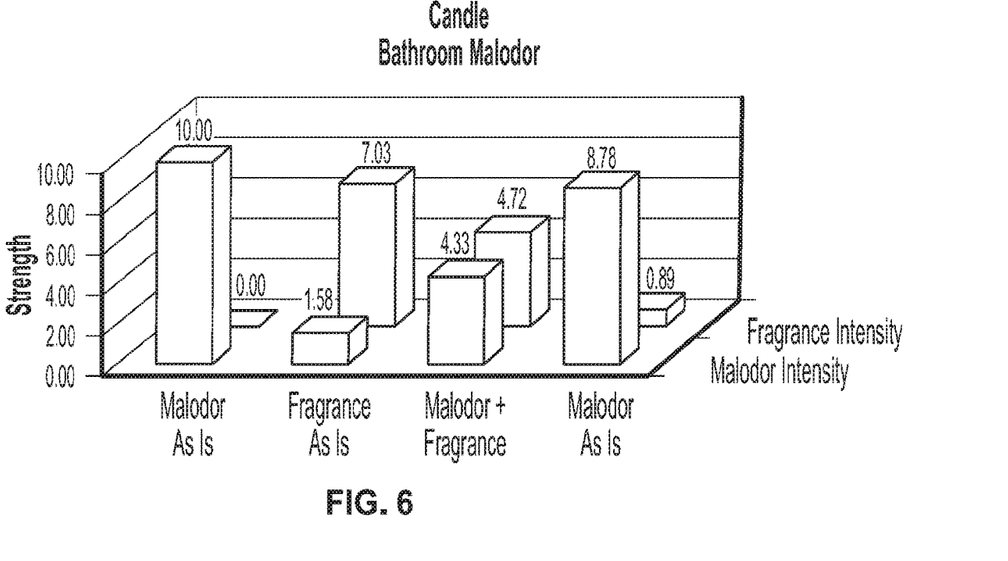
FIG. 6 shows an exemplary experimental set up and the observed malodor reduction, as reported by a sensory panel.

FIG. 6 shows exemplarily how the set up was conducted and the panel rated the malodor reduction. The pure malodor assessment (100%) known by the panelists is shown (left), as well as the pure fragrance (comprising 5 wt % fragrance containing 0.1 wt % lauryl methacrylate) (70.3%) unknown by the panelists as the second from left, the actual experiment as the third from left, and the pure malodor (87.8%) also unknown by the panelists on the right hand side. This number was normalized to 100% to calculate the reduction.

In order to assess the reduction of the kitchen malodor in the advanced experimental set up the complex pure malodor reference was placed in one of the qPOD® units. In the second unit the fragranced stearate gel (comprising 5 wt % fragrance containing 0.1 wt % lauryl methacrylate) (without malodor) was placed. In the third unit the malodor was placed along with the fragranced stearate gel (comprising 5 wt % fragrance containing 0.1 wt % lauryl methacrylate). In the fourth unit the pure malodor was placed again but this time unbeknownst to the panelists. It is important to note that this number was normalized to 100% and used as the reference line for any reduction. A rating system for the malodor of 0 (no malodor) to 10 (high level of malodor) as well as for the fragrance of 0 (no smell of fragrance) to 10 (strongest smell of fragrance) was applied. The sensory panel consisted of 15-20 people on average. There was a significant reduction by 29.6%. In this experiment the fragrance strength was assessed at 42.4%.

In order to assess the reduction of the bathroom malodor in the advanced experimental set up the complex pure malodor reference was placed in one of the qPOD® units. In the second unit the fragranced stearate gel (comprising 5 wt % fragrance containing 0.1 wt % lauryl methacrylate) (without malodor) was placed. In the third unit the malodor was placed along with the fragranced stearate gel (comprising 5 wt % fragrance containing 0.1 wt % lauryl methacrylate). In the fourth unit the pure malodor was placed again but this time unbeknownst to the panelists. It is important to note that this number was normalized to 100% and used as the reference line for any reduction. A rating system for the malodor of 0 (no malodor) to 10 (high level of malodor) as well as for the fragrance of 0 (no smell of fragrance) to 10 (strongest smell of fragrance) was applied. The sensory panel consisted of 15-20 people on average. There was a significant reduction by 22.5%. In this experiment the fragrance strength was assessed at 37.9%.

In order to assess the reduction of the kitchen malodor in the advanced experimental set up the complex pure malodor reference was placed in one of the qPOD® units. In the second unit the fragranced Reed Diffuser (comprising 18 wt % fragrance containing 0.1 wt % lauryl methacrylate) (without malodor) was placed. In the third unit the malodor was placed along with the fragranced Reed Diffuser (comprising 18 wt % fragrance containing 0.1 wt % lauryl methacrylate). In the fourth unit the pure malodor was placed again but this time unbeknownst to the panelists. It is important to note that this number was normalized to 100% and used as the reference line for any reduction. A rating system for the malodor of 0 (no malodor) to 10 (high level of malodor) as well as for the fragrance of 0 (no smell of fragrance) to 10 (strongest smell of fragrance) was applied. The sensory panel consisted of 15-20 people on average. There was a significant reduction by 36.0%. In this experiment the fragrance strength was assessed at 51.8%.

In order to assess the reduction of the bathroom malodor in the advanced experimental set up the complex pure malodor reference was placed in one of the qPOD® units. In the second unit the fragranced Reed Diffuser (comprising 18 wt % fragrance containing 0.1 wt % lauryl methacrylate) (without malodor) was placed by spraying it on two standard aerosol blotters (3×5 inches). In the third unit the malodor was placed along with the fragranced Reed Diffuser (comprising 18 wt % fragrance containing 0.1 wt % lauryl methacrylate). In the fourth unit the pure malodor was placed again but this time unbeknownst to the panelists. It is important to note that this number was normalized to 100% and used as the reference line for any reduction. A rating system for the malodor of 0 (no malodor) to 10 (high level of malodor) as well as for the fragrance of 0 (no smell of fragrance) to 10 (strongest smell of fragrance) was applied. The sensory panel consisted of 15-20 people on average. There was a significant reduction by 48.2%. In this experiment the fragrance strength was assessed at 61.0%.

In order to assess the reduction of the kitchen malodor in the advanced experimental set up the complex pure malodor reference was placed in one of the qPOD® units. In the second unit the fragranced room spray (comprising 5 wt % fragrance containing 0.1 wt % lauryl methacrylate) (without malodor) was placed. In the third unit the malodor was placed along with the fragranced room spray (comprising 5 wt % fragrance containing 0.1 wt % lauryl methacrylate) on the aerosol blotters. In the fourth unit the pure malodor was placed again but this time unbeknownst to the panelists. It is important to note that this number was normalized to 100% and used as the reference line for any reduction. A rating system for the malodor of 0 (no malodor) to 10 (high level of malodor) as well as for the fragrance of 0 (no smell of fragrance) to 10 (strongest smell of fragrance) was applied. The sensory panel consisted of 15-20 people on average. There was a significant reduction by 60.3%. In this experiment the fragrance strength was assessed at 52.1%.

Figure 7:
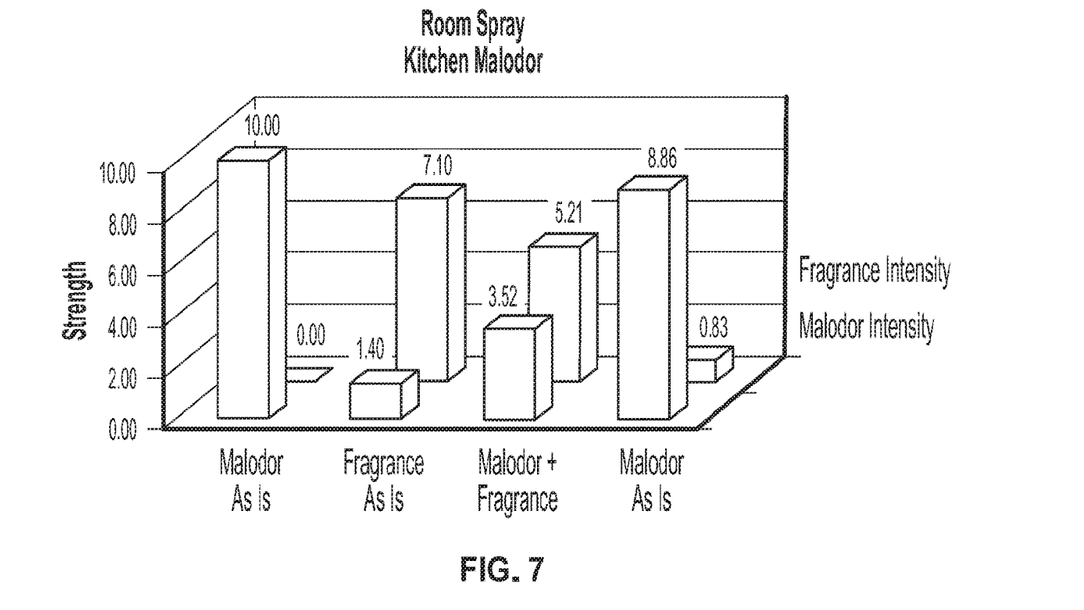
FIG. 7 shows an exemplary experimental set up and the observed malodor reduction, as reported by a sensory panel.

FIG. 7 shows exemplarily how the set up was conducted and the panel rated the malodor reduction. The pure malodor assessment (100%) known by the panelists is shown (left), as well as the pure fragrance (comprising 5 wt % fragrance containing 0.1 wt % lauryl methacrylate) (71.0%) unknown by the panelists as the second from left, the actual experiment as the third from left, and the pure malodor (88.6%) also unknown by the panelists on the right hand side. This number was normalized to 100% to calculate the reduction.

In order to assess the reduction of the bathroom malodor in the advanced experimental set up the complex pure malodor reference was placed in one of the qPOD® units. In the second unit the fragranced room spray (comprising 5 wt % fragrance containing 0.1 wt % lauryl methacrylate) (without malodor) was placed by spraying it on two standard aerosol blotters (3×5 inches). In the third unit the malodor was placed along with the fragranced room spray (comprising 5 wt % fragrance containing 0.1 wt % lauryl methacrylate) on the aerosol blotters. In the fourth unit the pure malodor was placed again but this time unbeknownst to the panelists. It is important to note that this number was normalized to 100% and used as the reference line for any reduction. A rating system for the malodor of 0 (no malodor) to 10 (high level of malodor) as well as for the fragrance of 0 (no smell of fragrance) to 10 (strongest smell of fragrance) was applied. The sensory panel consisted of 15-20 people on average. There was a significant reduction by 52.8%. In this experiment the fragrance strength was assessed at 55.8%.

Figure 8:
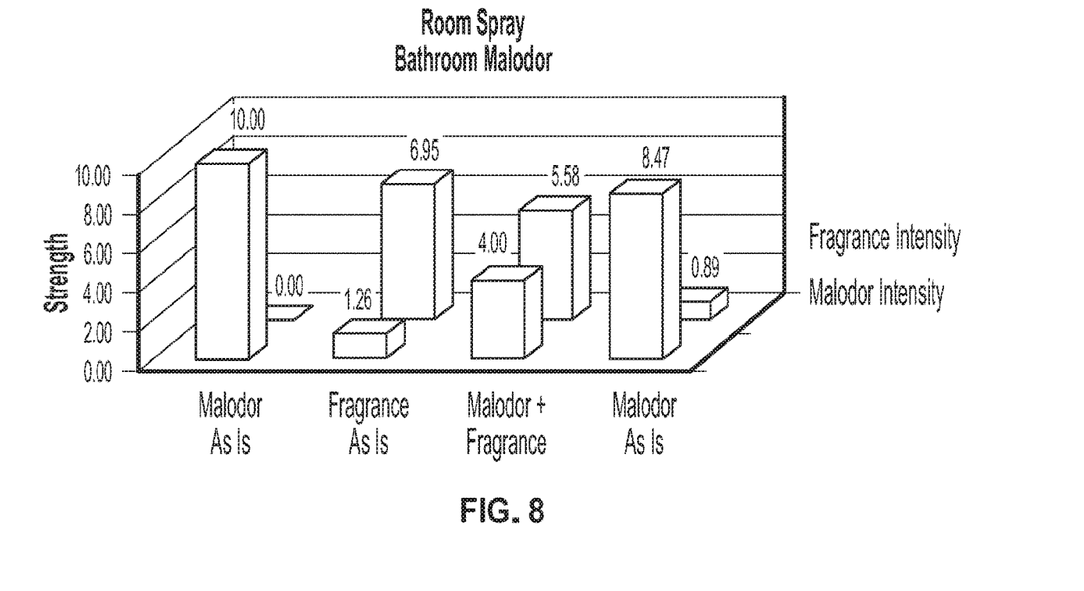
FIG. 8 shows an exemplary experimental set up and the observed malodor reduction, as reported by a sensory panel.

FIG. 8 shows exemplarily how the set up was conducted and the panel rated the malodor reduction. The pure malodor assessment (100%) known by the panelists is shown (left), as well as the pure fragrance (comprising 5 wt % fragrance containing 0.1 wt % lauryl methacrylate) (69.5%) unknown by the panelists as the second from left, the actual experiment as the third from left, and the pure malodor (84.7%) also unknown by the panelists on the right hand side. This number was normalized to 100% to calculate the reduction.

These advanced experiments confirm the early results and show that overall the respective malodor accords as part of the final fragrance work significantly to reduce kitchen and bathroom malodor. The conclusion from these experiments are interpreted in a way that the malodor reduction effect is achieved by the combination of active malodor reduction as well as 'masking' and/or chemically modifying the malodor by strong fragrance materials containing 0.1 wt % lauryl methacrylate. It is noteworthy that the panelists didn't rate the pure malodor as high enough anymore when it was unknown to them what exactly had been placed in the qPOD® unit #4. In order to take this 'psychological' effect into account the respective numbers of unit #4 were normalized to 100%. The respective numbers of unit #3 (actual experiments) for the malodor reduction were corrected accordingly.

Figure 9:
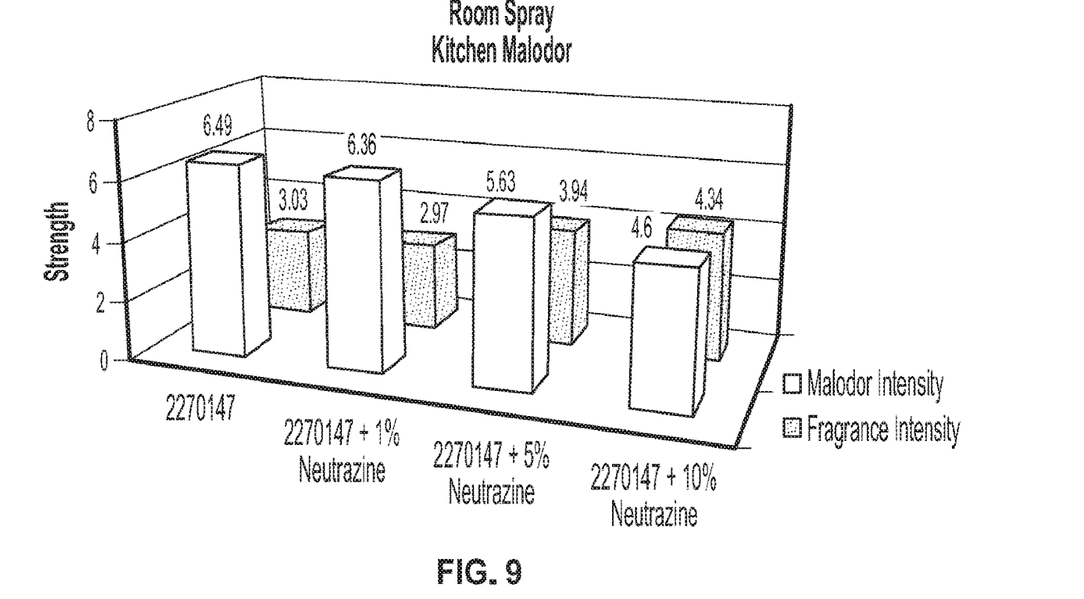
FIG. 9 shows an exemplary experimental set up and the observed malodor reduction, as reported by a sensory panel.
Figure 10:
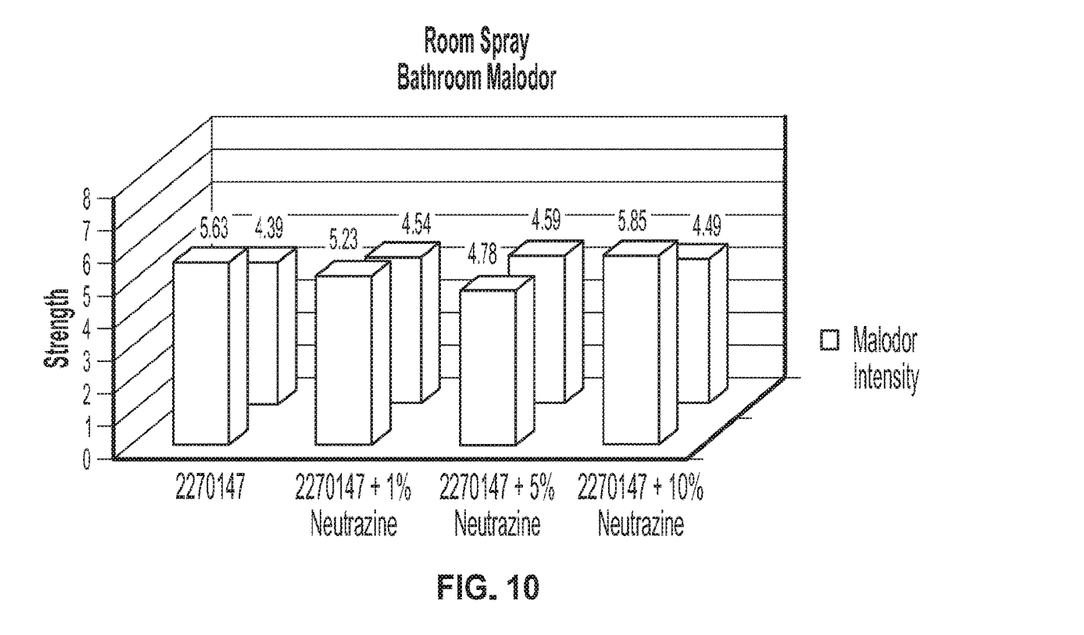
FIG. 10 shows an exemplary experimental set up and the observed malodor reduction, as reported by a sensory panel.

Example 4: Malodor Reduction Using Compositions According to Certain Aspects Presented Herein In this example, fragrance formulations containing either 1, 5, or 10 wt % lauryl methacrylate were constructed, and the ability of the formulations, used in a room spray at a 5% w/w concentration to reduce the perception of kitchen or bathroom malodors was evaluated. The results are shown in FIGS. 9 and 10 respectively.

Taken together, these data suggest that lauryl methacrylate reduces the perception of malodor in a dose dependent manner. However, lauryl methacrylate alone at 0.5% was less able to reduce the perception of malodor, compared to the reduction in malodor observed in formulations containing a fragrance and lauryl methacrylate.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an aspect" or "one aspect" means that a particular feature, structure, or characteristic described in connection with the aspect is included in at least one aspect. Thus, the appearances of the phrase "an aspect" or "one aspect" in various places throughout this specification are not necessarily all referring to the same aspect.

Publications cited throughout this document are hereby incorporated by reference in their entirety. Although the various aspects of the invention have been illustrated above by reference to examples and preferred aspects, it will be appreciated that the scope of the invention is defined not by the foregoing description but by the following claims properly construed under principles of patent law.

What is claimed is:

1. A scented candle comprising a composition comprising:
   a. a malodor reducing component comprising lauryl methacrylate; and
   b. a freshening fragrance component selected from the group consisting of adoxal (2,6,10-trimethyl-9-undecenal), aldehyde C-8, aldehyde C-9, aldehyde C-10, aldehyde C-11, aldehyde C-12, aldehyde C-14, aldehyde C-16, aldehyde C-18, allyl amyl glycolate, allyl cyclohexyl propionate, allyl heptanoate, amyl acetate, ambretone, ambroxan, amyl salicylate, bacdanol, basil oil, benzaldehyde, borneol, bourgeonal (4-t-butylbenzenepropionaldehyde), buchu leaf oil, cashmeran, cedar leaf oil, cinnamic alcohol, cinnamic aldehyde, citral, citrathal, citronellal (3,7-dimethyl 6-octenal), citronellol, citronellyl nitrile, citronitrile, clonal, coumarin, cyclal (2,4-dimethyl-3-cyclohexen-1-carbaldehyde), cyclacet, cyclamen aldehyde (cyclamal), cyclaprop, cymal, cyclosal, cyclopentadecanone, damascenone, delta-damascone, gamma-declalactone, trans-2-decenal, cis-4-decenal, diethyl malonate, dihydrojasmone, dihydromyrcenol, dihydromyrcenyl acetate, dimethyl benzyl carbonyl butyrate, dimetol, dioctyl adipate, trans-2-dodecenal, dupical, dynascone, ethyl acetate, ethyl butyrate, ethyl linaly acetate, ethyl vanillin, ethyl linalyl acetate, ethylene brassylate, ethyl butyrate, ethyl caprylate, eugenol, florhydral (3-(3-isopropyl-phenyl)-butyraldehyde), floralozone, florhydral, fructone, galaxolide, geraniol, geranium oil, geranyl acetate, hedione, helional (alpha-methyl-3,4-(methylenedioxy)-hydrocinnamaldehyde), hercolyn D, hexadecanolide, cis-3-hexenyl acetate, hexyl acetate, hexyl cinnamic aldehyde, hexyl salicylate, hydrocinnamaldehyde (3-phenylpropanal), hydroxycitronellal, hydroxycitronellol, indoflor, alpha-ionone, beta ionone, isobutylquinoline, iso cyclo citral, iso E super, isoeugenol, isofragrarone, karanal, lavender oil, lavendin oil, lime aldehyde (alpha-methyl-p-isopropyl phenyl propyl aldehyde), limonene, lilial (2-methyl-4-t-butylphenyl)propanal), linalool, linalyl acetate, linalooloxide, lyral (4-(4-hydroxy-4-methylpentyl)-3-cyclohexene-1-carboxaldehyde), manzanate, melonal (2,6-dimethyl-5-heptenal), methoxy melonal (6-methoxy-2,6-dimethyl-heptanal), methyl acetophenone, methyl anthranilate, alpha-methyl ionone, gamma-methyl ionone, methyl salicylate, methyl nonyl acetaldehyde, 2-methylundecenal (C-12 MNA), myrac aldehyde, 2,6-nonadienal, 2,6-nonadienol, orange terpenes, orange oil, oxane, oxyoctaline formate, oxyphenylon, ozonil, patchouli oil, petitgrain oil, petiole, phenylacetaldehyde, phenylethanol, pino acetaldehyde, precyclemone B, polysantol, raspberry ketone, rose crystals, rosemary oil, scentenal, sinensal, spirogalbanone, styrallyl acetate, tangerinol, tetrahydrolinalyl acetate, tetrahydromyrcenol, para-tolylaldehyde, tricyclodecylidenebutanal tridecene-2-nitrile, triplal, vanillin, vernaldehyde, vertocitral (2,4-dimethyl-3-cyclohexene-1-carboxaldehyde), verdox, vertenex, violet nitrile, yara yara, ylang, and combinations thereof;

or a composition comprising:
   a. a malodor reducing component comprising lauryl methacrylate;
   b. one or more esters present from 5% to 80% by weight;
   c. one or more aldehydes present from 5% to 55% by weight;
   d. one or more alcohols present from 5% to 70% by weight;
   e. one or more ketones present from 0.1% to 15% by weight;
   f. one or more lactones present from 0.1% to 15% by weight; and
   g. one or more nitriles present from 0.1% to 10% by weight.

2. A scented gel comprising:
a. stearate; and
b. a composition comprising:
   a'. a malodor reducing component comprising lauryl methacrylate; and
   b'. a freshening fragrance component selected from the group consisting of adoxal (2,6,10-trimethyl-9-undecenal), aldehyde C-8, aldehyde C-9, aldehyde C-10, aldehyde C-11, aldehyde C-12, aldehyde C-14, aldehyde C-16, aldehyde C-18, allyl amyl glycolate, allyl cyclohexyl propionate, allyl heptanoate, amyl acetate, ambretone, ambroxan, amyl salicylate, bacdanol, basil oil, benzaldehyde, borneol, bourgeonal (4-t-butylbenzenepropionaldehyde), buchu leaf oil, cashmeran, cedar leaf oil, cinnamic alcohol, cinnamic aldehyde, citral, citrathal, citronellal (3,7-dimethyl 6-octenal), citronellol, citronellyl nitrile, citronitrile, clonal, coumarin, cyclal (2,4-dimethyl-3-cyclohexen-1-carbaldehyde), cyclacet, cyclamen aldehyde (cyclamal), cyclaprop, cymal, cyclosal, cyclopentadecanone, damascenone, delta-damascone, gamma-declalactone, trans-2-decenal, cis-4-decenal, diethyl malonate, dihydrojasmone, dihydromyrcenol, dihydromyrcenyl acetate, dimethyl benzyl carbonyl butyrate, dimetol, dioctyl adipate, trans-2-dodecenal, dupical, dynascone, ethyl acetate, ethyl butyrate, ethyl linaly acetate, ethyl vanillin, ethyl linalyl acetate, ethylene brassylate, ethyl butyrate, ethyl caprylate, eugenol, florhydral (3-(3-isopropyl-phenyl)-butyraldehyde), floralozone, florhydral, fructone, galaxolide, geraniol, geranium oil, geranyl acetate, hedione, helional (alpha-methyl-3,4-(methylenedioxy)-hydrocinnamaldehyde), hercolyn D, hexadecanolide, cis-3-hexenyl acetate, hexyl acetate, hexyl cinnamic aldehyde, hexyl salicylate, hydrocinnamaldehyde (3-phenylpropanal), hydroxycitronellal, hydroxycitronellol, indoflor, alpha-ionone, beta ionone, isobutylquinoline, iso cyclo citral, iso E super, isoeugenol, isofragrarone, karanal, lavender oil, lavendin oil, lime aldehyde (alpha-methyl-p-isopropyl phenyl propyl aldehyde), limonene, lilial (2-methyl-4-t-butylphenyl)propanal), linalool, linalyl acetate, linalooloxide, lyral (4-(4-hydroxy-4-methylpentyl)-3-cyclohexene-1-carboxaldehyde), manzanate, melonal (2,6-dimethyl-5-heptenal), methoxy melonal (6-methoxy-2,6-dimethylheptanal), methyl acetophenone, methyl anthranilate, alpha-methyl ionone, gamma-methyl ionone, methyl salicylate, methyl nonyl acetaldehyde, 2-methylundecenal (C-12 MNA), myrac aldehyde, 2,6-nonadienal, 2,6-nonadienol, orange terpenes, orange oil, oxane, oxyoctaline formate, oxyphenylon, ozonil, patchouli oil, petitgrain oil, petiole, phenylacetaldehyde, phenylethanol, pino acetaldehyde, precyclemone B, polysantol, raspberry ketone, rose crystals, rosemary oil, scentenal, sinensal, spirogalbanone, styrallyl acetate, tangerinol, tetrahydrolinalyl acetate, tetrahydromyrcenol, para-tolylaldehyde, tricyclodecylidenebutanal tridecene-2-nitrile, triplal, vanillin, vernaldehyde, vertocitral (2,4-dimethyl-3-cyclohexene-1-carboxaldehyde), verdox, vertenex, violet nitrile, yara yara, ylang, and combinations thereof;
or a composition comprising:
   a'. a malodor reducing component comprising lauryl methacrylate;
   b'. one or more esters present from 5% to 80% by weight;
   c'. one or more aldehydes present from 5% to 55% by weight;
   d'. one or more alcohols present from 5% to 70% by weight;
   e'. one or more ketones present from 0.1% to 15% by weight;
   f'. one or more lactones present from 0.1% to 15% by weight; and
   g'. one or more nitriles present from 0.1% to 10% by weight.

3. A method of reducing malodor in air care applications, the method comprising applying to a kitchen, a living room, an office, a bathroom, a lobby, or a trash room a scented candle or a scented gel,
wherein the scented candle comprises a composition comprising:
a. a malodor reducing component comprising lauryl methacrylate; and
b. a freshening fragrance component selected from the group consisting of adoxal (2,6,10-trimethyl-9-undecenal), aldehyde C-8, aldehyde C-9, aldehyde C-10, aldehyde C-11, aldehyde C-12, aldehyde C-14, aldehyde C-16, aldehyde C-18, allyl amyl glycolate, allyl cyclohexyl propionate, allyl heptanoate, amyl acetate, ambretone, ambroxan, amyl salicylate, bacdanol, basil oil, benzaldehyde, borneol, bourgeonal (4-t-butylbenzenepropionaldehyde), buchu leaf oil, cashmeran, cedar leaf oil, cinnamic alcohol, cinnamic aldehyde, citral, citrathal, citronellal (3,7-dimethyl 6-octenal), citronellol, citronellyl nitrile, citronitrile, clonal, coumarin, cyclal (2,4-dimethyl-3-cyclohexen-1-carbaldehyde), cyclacet, cyclamen aldehyde (cyclamal), cyclaprop, cymal, cyclosal, cyclopentadecanone, damascenone, delta-damascone, gamma-declalactone, trans-2-decenal, cis-4-decenal, diethyl malonate, dihydrojasmone, dihydromyrcenol, dihydromyrcenyl acetate, dimethyl benzyl carbonyl butyrate, dimetol, dioctyl adipate, trans-2-dodecenal, dupical, dynascone, ethyl acetate, ethyl butyrate, ethyl linaly acetate, ethyl vanillin, ethyl linalyl acetate, ethylene brassylate, ethyl butyrate, ethyl caprylate, eugenol, florhydral (3-(3-isopropyl-phenyl)-butyraldehyde), floralozone, florhydral, fructone, galaxolide, geraniol, geranium oil, geranyl acetate, hedione, helional (alpha-methyl-3,4-(methylenedioxy)-hydrocinnamaldehyde), hercolyn D, hexadecanolide, cis-3-hexenyl acetate, hexyl acetate, hexyl cinnamic aldehyde, hexyl salicylate, hydrocinnamaldehyde (3-phenylpropanal), hydroxycitronellal, hydroxycitronellol, indoflor, alpha-ionone, beta ionone, isobutylquinoline, iso cyclo citral, iso E super, isoeugenol, isofragrarone, karanal, lavender oil, lavendin oil, lime aldehyde (alpha-methyl-p-isopropyl phenyl propyl aldehyde), limonene, lilial (2-methyl-4-t-butylphenyl)propanal), linalool, linalyl acetate, linalooloxide, lyral (4-(4-hydroxy-4-methylpentyl)-3-cyclohexene-1-carboxaldehyde), manzanate, melonal (2,6-dimethyl-5-heptenal), methoxy melonal (6-methoxy-2,6-dimethylheptanal), methyl acetophenone, methyl anthranilate, alpha-methyl ionone, gamma-methyl ionone, methyl salicylate, methyl nonyl acetaldehyde, 2-methylundecenal (C-12 MNA), myrac aldehyde, 2,6-nonadienal, 2,6-nonadienol, orange terpenes, orange oil, oxane, oxyoctaline formate, oxyphenylon, ozonil, patchouli oil, petitgrain oil, petiole, phenylacetaldehyde, phenylethanol, pino acetaldehyde, precyclemone B, polysantol, raspberry ketone, rose crystals, rosemary oil, scentenal, sinensal, spirogalbanone, styrallyl acetate, tangerinol, tetrahydrolinalyl acetate, tetrahydromyrcenol, para-tolylaldehyde, tricyclodecylidenebutanal tridecene-2-nitrile, triplal, vanillin, vernaldehyde, vertocitral (2,4-dimethyl-3-cyclohexene-1-carboxaldehyde), verdox, vertenex, violet nitrile, yara yara, ylang, and combinations thereof;

or a composition comprising:
 a. a malodor reducing component comprising lauryl methacrylate;
 b. one or more esters present from 5% to 80% by weight;
 c. one or more aldehydes present from 5% to 55% by weight;
 d. one or more alcohols present from 5% to 70% by weight;
 e. one or more ketones present from 0.1% to 15% by weight;
 f. one or more lactones present from 0.1% to 15% by weight; and
 g. one or more nitriles present from 0.1% to 10% by weight;

and
wherein the scented gel comprises:
 a. stearate; and
 b. a composition comprising:
  a'. a malodor reducing component comprising lauryl methacrylate; and
  b'. a freshening fragrance component selected from the group consisting of adoxal (2,6,10-trimethyl-9-undecenal), aldehyde C-8, aldehyde C-9, aldehyde C-10, aldehyde C-11, aldehyde C-12, aldehyde C-14, aldehyde C-16, aldehyde C-18, allyl amyl glycolate, allyl cyclohexyl propionate, allyl heptanoate, amyl acetate, ambretone, ambroxan, amyl salicylate, bacdanol, basil oil, benzaldehyde, borneol, bourgeonal (4-t-butylbenzenepropionaldehyde), buchu leaf oil, cashmeran, cedar leaf oil, cinnamic alcohol, cinnamic aldehyde, citral, citrathal, citronellal (3,7-dimethyl 6-octenal), citronellol, citronellyl nitrile, citronitrile, clonal, coumarin, cyclal (2,4-dimethyl-3-cyclohexen-1-carbaldehyde), cyclacet, cyclamen aldehyde (cyclamal), cyclaprop, cymal, cyclosal, cyclopentadecanone, damascenone, delta-damascone, gamma-declalactone, trans-2-decenal, cis-4-decenal, diethyl malonate, dihydrojasmone, dihydromyrcenol, dihydromyrcenyl acetate, dimethyl benzyl carbonyl butyrate, dimetol, dioctyl adipate, trans-2-dodecenal, dupical, dynascone, ethyl acetate, ethyl butyrate, ethyl linaly acetate, ethyl vanillin, ethyl linalyl acetate, ethylene brassylate, ethyl butyrate, ethyl caprylate, eugenol, florhydral (3-(3-isopropylphenyl)-butyraldehyde), floralozone, florhydral, fructone, galaxolide, geraniol, geranium oil, geranyl acetate, hedione, helional (alpha-methyl-3,4-(methylenedioxy)-hydrocinnamaldehyde), hercolyn D, hexadecanolide, cis-3-hexenyl acetate, hexyl acetate, hexyl cinnamic aldehyde, hexyl salicylate, hydrocinnamaldehyde (3-phenylpropanal), hydroxycitronellal, hydroxycitronellol, indoflor, alpha-ionone, beta ionone, isobutylquinoline, iso cyclo citral, iso E super, isoeugenol, isofragrarone, karanal, lavender oil, lavendin oil, lime aldehyde (alpha-methyl-p-isopropyl phenyl propyl aldehyde), limonene, lilial (2-methyl-4-t-butylphenyl)propanal), linalool, linalyl acetate, linalooloxide, lyral (4-(4-hydroxy-4-methylpentyl)-3-cyclohexene-1-carboxaldehyde), manzanate, melonal (2,6-dimethyl-5-heptenal), methoxy melonal (6-methoxy-2,6-dimethylheptanal), methyl acetophenone, methyl anthranilate, alpha-methyl ionone, gamma-methyl ionone, methyl salicylate, methyl nonyl acetaldehyde, 2-methylundecenal (C-12 MNA), myrac aldehyde, 2,6-nonadienal, 2,6-nonadienol, orange terpenes, orange oil, oxane, oxyoctaline formate, oxyphenylon, ozonil, patchouli oil, petitgrain oil, petiole, phenylacetaldehyde, phenylethanol, pino acetaldehyde, precyclemone B, polysantol, raspberry ketone, rose crystals, rosemary oil, scentenal, sinensal, spirogalbanone, styrallyl acetate, tangerinol, tetrahydrolinalyl acetate, tetrahydromyrcenol, para-tolylaldehyde, tricyclodecylidenebutanal tridecene-2-nitrile, triplal, vanillin, vernaldehyde, vertocitral (2,4-dimethyl-3-cyclohexene-1-carboxaldehyde), verdox, vertenex, violet nitrile, yara yara, ylang, and combinations thereof;

or a composition comprising:
 a'. a malodor reducing component comprising lauryl methacrylate;
 b'. one or more esters present from 5% to 80% by weight;
 c'. one or more aldehydes present from 5% to 55% by weight;
 d'. one or more alcohols present from 5% to 70% by weight;
 e'. one or more ketones present from 0.1% to 15% by weight;
 f'. one or more lactones present from 0.1% to 15% by weight; and
 g'. one or more nitriles present from 0.1% to 10% by weight.

4. The method according to claim 3, wherein the lauryl methacrylate concentration is from 0.5 to 2%.

* * * * *